US012746071B2

(12) United States Patent
Saur et al.

(10) Patent No.: US 12,746,071 B2
(45) Date of Patent: Sep. 29, 2026

(54) COMPUTER-IMPEMENTED METHOD FOR DETERMINING A TRANSFORMATION SPECIFICATION WITH PREOPERATIVE IMAGE DATA USING SEARCH IMAGES FROM A SURGICAL MICROSCOPE

(71) Applicant: CARL ZEISS MEDITEC AG, Jena (DE)

(72) Inventors: Stefan Saur, Aalen (DE); Christoph Hauger, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 83 days.

(21) Appl. No.: 18/726,409

(22) PCT Filed: Dec. 29, 2022

(86) PCT No.: PCT/EP2022/088028
§ 371 (c)(1),
(2) Date: Jul. 3, 2024

(87) PCT Pub. No.: WO2023/135022
PCT Pub. Date: Jul. 20, 2023

(65) Prior Publication Data

US 2025/0072977 A1 Mar. 6, 2025

(30) Foreign Application Priority Data

Jan. 12, 2022 (DE) ..................... 10 2022 100 626.3

(51) Int. Cl.
*A61B 34/20* (2016.01)
*G06T 7/00* (2017.01)
*G06T 7/80* (2017.01)

(52) U.S. Cl.
CPC ............ *A61B 34/20* (2016.02); *G06T 7/0014* (2013.01); *G06T 7/80* (2017.01); *A61B 2034/2065* (2016.02)

(58) Field of Classification Search
CPC . A61B 34/20; A61B 2034/2065; A61B 34/30; A61B 90/96; A61B 2090/371;
(Continued)

(56) References Cited

U.S. PATENT DOCUMENTS

| | | | |
|---|---|---|---|
| 5,795,294 | A | 8/1998 | Luber et al. |
| 7,561,733 | B2 | 7/2009 | Vilsmeier et al. |

(Continued)

FOREIGN PATENT DOCUMENTS

| | | | |
|---|---|---|---|
| CN | 101090678 | A | 12/2007 |
| CN | 113616331 | A | 11/2021 |

(Continued)

OTHER PUBLICATIONS

International Preliminary Report on Patentability for Application No. PCT/EP2022/088028, dated Jul. 12, 2024 (15 pages) (with machine translation).

(Continued)

*Primary Examiner* — Serkan Akar
*Assistant Examiner* — Jason P Gross
(74) *Attorney, Agent, or Firm* — NIXON PEABODY LLP; Jeffrey L. Costellia

(57) ABSTRACT

Various examples relate to techniques for recording, in association with surgery carried out on a patient, measurement data with depth resolution, such that, on the basis thereof, it is possible to determine a transformation specification which mediates between images captured by means of a robotic visualization system, e.g. a surgical microscope, and preoperative volume image data.

20 Claims, 4 Drawing Sheets

(58) Field of Classification Search
CPC . A61B 90/361; A61B 90/25; A61B 2090/364; A61B 2090/3945; A61B 90/20; G06T 7/0014; G06T 7/80
See application file for complete search history.

(56) References Cited

U.S. PATENT DOCUMENTS

| | | | | |
|---|---|---|---|---|
| 2007/0238981 | A1 | 10/2007 | Zhu et al. | |
| 2007/0270690 | A1 | 11/2007 | Woerlein | |
| 2015/0348311 | A1 | 12/2015 | Saur et al. | |
| 2017/0085855 | A1* | 3/2017 | Roberts | H04N 13/257 |
| 2017/0224298 | A1* | 8/2017 | Hannemann | A61B 6/469 |
| 2019/0324252 | A1* | 10/2019 | Mak | G02B 21/06 |
| 2021/0145523 | A1* | 5/2021 | Xing | G06T 7/73 |
| 2022/0215532 | A1* | 7/2022 | Aghdasi | G06T 7/30 |
| 2023/0196595 | A1* | 6/2023 | Grupp, Jr. | G06T 17/00 382/294 |

FOREIGN PATENT DOCUMENTS

| | | | |
|---|---|---|---|
| DE | 102014210051 | A1 | 12/2015 |
| DE | 102014216718 | A1 | 2/2016 |
| WO | 2021087433 | A1 | 5/2021 |

OTHER PUBLICATIONS

International Search Report for Application No. PCT/EP2022/088028, mailed Mar. 16, 2023 (4 pages) (with machine translation).
Written Opinion for Application No. PCT/EP2022/088028, mailed Mar. 16, 2023 (9 pages) (with machine translation).

* cited by examiner

COMPUTER-IMPEMENTED METHOD FOR DETERMINING A TRANSFORMATION SPECIFICATION WITH PREOPERATIVE IMAGE DATA USING SEARCH IMAGES FROM A SURGICAL MICROSCOPE

CROSS-REFERENCE TO RELATED APPLICATIONS

The present application is the U.S. National Stage entry of International Application No. PCT/EP2022/088028, filed Dec. 29, 2022, which claims priority under 35 U.S.C. § 119 to German Patent Application No. 10 2022 100 626.3, filed Jan. 12, 2022, the contents of which are incorporated by reference herein in their entirety.

TECHNICAL FIELD

Various examples relate to techniques for capturing measurement data with depth resolution for a target region, wherein by means of the measurement data with depth resolution it is possible to determine a transformation specification between image data captured by means of a robotic visualization system and preoperative volume image data.

BACKGROUND

In order that for navigation applications in microsurgery, for example, preoperative volume image data (e.g. computed tomography, CT, or magnetic resonance imaging, MRI) can be superimposed on the patient's anatomy spatially accurately during the surgery, registration of the preoperative image data relative to the patient's position during the surgery is necessary, that is to say that a transformation specification is determined which describes how preoperative image data have to be transformed in order to be able to be superimposed on the patient spatially accurately.

Determining the transformation specification requires corresponding points in the preoperative volume image data and from the patient in the operating room. The transformation specification maps images captured by means of a robotic visualization system in the operating room onto preoperative volume image data, and/or vice versa.

In some examples, physical markers are attached to the patient for this purpose, which are visible both in the preoperative volume image data and in image data of a visualization system in the operating room. What is disadvantageous about this approach is that the physical markers have to be attached to the patient, which is prone to error and laborious. Moreover, it is necessary to attach the physical markers to the patient or stationarily in relation to the patient both for the recording of the preoperative volume image data and before the actual surgery.

A markerless approach is taken in other examples. In that case, the geometry of the surface (topography of the anatomy) of a target region of the patient is visible both in measurement data which are captured in the operating room and have a depth resolution, and in the preoperative image data:

By way of example, using a hand-portable pointer instrument, significant points of the skull geometry (base of the ear, cheeks, nose, . . . ) can be touched and the corresponding measurement points (which are then defined in three-dimensional space) of the measurement data obtained in this way can be transmitted to the navigation system. This gives rise to sparse sampling of the surface of the skull which is registered relative to the surface which was obtained from a preoperative data set. Such techniques require additional hardware and are associated with a certain time expenditure in order to capture the measurement data by operating the pointer instrument.

In order to capture the surface more extensively, more rapidly and without additional hardware, methods have been proposed which use stereoscopic image data of a robotic visualization system (e.g. surgical microscope) in order to determine the surface of the patient's head therefrom. See e.g. U.S. Pat. No. 7,561,733B2 or DE102014210051A1. However, these methods presuppose that the robotic visualization system is already aligned with the patient, such that the stereoscopic image data image the target region which allows registration. This is not given in the normal case, however, since this information would only be available after registration of the patient. Manual alignment may therefore be necessary, which is in turn laborious and prone to error.

BRIEF SUMMARY

There is a need for improved techniques for making it possible to determine a transformation specification between images captured by means of a robotic visualization system and preoperative volume image data of the patient. In particular, there is a need for techniques which eliminate or reduce the abovementioned disadvantages and limitations of previously known techniques.

This object is achieved by the features of the independent patent claims. The features of the dependent patent claims define embodiments.

Rapid and efficient registration of the patient is possible by means of the techniques described herein. That means that the transformation specification can be determined reliably and in an automated manner. The target region for which measurement data are captured with depth resolution in order to determine the transformation specification in this way can be found and recognized in an automated manner.

The techniques described herein thus make it possible to register preoperative volume image data in a reference coordinate system associated with images that are captured by means of a robotic visualization system.

A computer-implemented method comprises actuating a robotic visualization system in order to record at least one search image in this way. The at least one search image at least partly images a patient. Moreover, the method also comprises determining an arrangement of a target region in the at least one search image. Furthermore, the method comprises actuating the robotic visualization system for recording measurement data with depth resolution based on the arrangement of the target region in the at least one search image. In this case, the measurement data are indicative of a topography of an anatomy of the patient. The measurement data make it possible to determine a transformation specification between images recorded by means of the robotic visualization system and preoperative volume image data of the patient.

The target region can denote a region of the patient for which the preoperative volume image data are available. The preoperative volume image data can thus also be indicative of the topography of the anatomy of the patient in the area of the target region. By way of example, the target region could denote an intervention area of planned surgery. The target region could comprise a patient's head, for example. The target region could comprise part of a patient's head.

The arrangement of the target region can denote a position and/or orientation and/or shape and/or size of the target region.

Recording the at least one search image by means of the robotic visualization system thus makes it possible to search for and recognize the target region.

Manually finding the target region, for example by way of manual positioning of the robotic visualization system, can be obviated. An automatic alignment of the robotic visualization system, such that the measurement data can be captured as observables for the topography of the patient's anatomy in the target region, is made possible based on the determined arrangement of the target region in the at least one search image.

The preoperative volume image data could be CT image data or MR image data, for example. They could also be positron emission tomography image data.

By way of example, it would be conceivable for an individual search image to be captured by means of the robotic visualization system. In particular, for example, an overview image could be captured by means of a corresponding camera of an overview-image imaging unit which uses a lens that provides no or a comparatively low magnification. In such a case, the search image could image the target region and further surrounding areas. During typical surgery in the area of the patient's head, for example, the patient's head could be imaged down to the chest area or down to the torso or hip area.

In other examples, it would also be conceivable for a plurality of search images to be recorded, wherein each search image images a different area. A grid of search images could be captured.

By way of example, the robotic visualization system could be actuated in order to record at least one search image sequence. Each of the at least one search image sequence can comprise a plurality of corresponding search images.

That means that the search images can be captured in one or two (or more) sequences in one stage or in two stages, for example.

By way of example, the search region respectively associated with the respective search image sequence could be adapted or in particular refined from search image sequence to search image sequence. By way of example, the search images of different search image sequences could have different resolutions. By way of example, the search images of different search image sequences could have an increasing magnification.

By way of example, the search images of a search image sequence could scan a corresponding search region. For this purpose, at least one motor of the robotic visualization system could be actuated during the recording of the at least one search image sequence in order to reposition the robotic visualization system a number of times.

By way of example, a corresponding optical system and camera of an imaging unit used to capture the search images could be attached to a microscope head of a surgical microscope, wherein the microscope head is positionable in space by way of a stand with one or more movable axes, for example translationally and/or rotationally.

A comparatively large search region can be covered by the scanning. A relatively large magnification can nevertheless be used at the same time, such that the target region can be reliably recognized.

By way of example, a first search region can be assigned to a first search image sequence of the at least one search image sequence, and a second search region can be assigned to a second search image sequence of the at least one search image sequence.

The second search region could be included in the first search region. The second search region could also be partly different than the first search region.

The robotic visualization system can then be actuated in order firstly to record the first search image sequence and subsequently to record the second search image sequence.

The method can comprise evaluating the one or more search images of the first search image sequence. Based on this evaluating, it is then possible to determine values for at least one imaging parameter of the robotic visualization system which is used for recording the second search image sequence.

As a general rule, imaging parameters can denote the spatial arrangement of the imaging unit, used to capture the corresponding images, of the robotic visualization system and/or also the parameterization of the imaging chain (zoom, focus, light, exposure parameters, etc.). Imaging parameters can therefore be such parameters which influence the appearance of an image and/or the field of view of an image.

Such techniques therefore make it possible to carry out a situation-specific adaptation of values for at least one imaging parameter. Depending on the specific situation in connection with the visualization of the respective patient, the values for the at least one imaging parameter can be suitably adapted, such that the target region can be found reliably by means of the search images of the second search image sequence.

By way of example, evaluating the one or more search images of the first search image sequence could comprise determining an arrangement of a marker stationarily fixed with respect to the patient in the one or more search images of the search image sequence. The values for the at least one imaging parameter could then be determined based on the arrangement of the marker stationarily fixed with respect to the patient.

By way of example, the arrangement of the second search region in relation to the first search region could be determined by setting the fields of view of the search images of the second search region. By way of example, the relative arrangement of the marker in relation to the target region could be previously known, in principle. The marker could be attached to the patient for example by means of a clamp or other fixing means, in a manner offset with respect to the target region. This offset can be known. The second search region could then be arranged in relative relation to the first search region or to the marker found in the search images of the first search region.

A further exemplary implementation of the evaluation of the one or more search images of the first search image sequence can comprise for example ascertaining values for one or more illumination parameters for recording the second search image sequence. In this regard, it would be conceivable, for example, to evaluate brightness histograms for the one or more search images of the first search image sequence and then to set the exposure duration and/or the brightness of an illumination for recording the one or more search images of the second search image sequence, such that the brightness histograms for the one or more search images of the second search image sequence correspond to a target predefinition. In this way, it is possible to ensure that the contrast used for imaging specific anatomical features or skin tissue, for example, in the one or more search images of the second search image sequence images details for finding the target region.

In further examples, it would also be conceivable for evaluating the one or more search images of the first search image sequence to be taken as a basis for determining whether one or more search images of the first search image sequence can be reused for the second search image sequence.

For example, if the second search region for the second search image sequence is determined in such a way that this has an overlap with the first search region of the first search image sequence, then in a corresponding overlap area search images that have already been recorded for the first search image sequence could be reused for the second search image sequence, too. The time period required for capturing the search images can be reduced in this way.

Put generally, it is conceivable for at least one search image to be both part of the first search image sequence and part of the second search image sequence.

By way of example, it would be conceivable to evaluate the second search image sequence in order to recognize skin tissue of the patient in the one or more search images of the second search image sequence. The arrangement of the target region could then be determined based on recognizing the skin tissue.

The patient is typically covered for the most part, for example by a surgical drape. Just the target region and immediately surrounding areas may be exposed. The target region can therefore be recognized by means of the recognition of skin tissue.

The method can comprise receiving tracking data from a tracking system. The tracking system can be collocated with respect to the robotic visualization system. That means that the robotic visualization system and the tracking system can operate in a common reference coordinate system or the tracking system can be used to determine the arrangement of the robotic visualization system (and thus also the pose or the field of view of measurement data or images captured by means of the robotic visualization system) in the reference coordinate system. The tracking system can also be configured to determine the arrangement (that is to say the position and/or orientation) of other markers in the reference coordinate system. The reference coordinate system can be determined in relation to the operating room.

The tracking data could describe for example an arrangement of a marker stationarily fixed with respect to the patient in relation to the robotic visualization system. The marker can be implemented e.g. by passive machine-readable symbols or active machine-readable light sources.

Accordingly, the method could furthermore comprise determining values for at least one imaging parameter of the robotic visualization system which is used for recording the at least one search image sequence, based on the tracking data.

By way of example, an arrangement of a corresponding search region covered by the at least one search image sequence could be determined based on the tracking data. If the marker is recognized by means of the tracking system, for example, then the relative positioning of the marker in relation to the target region can be previously known.

Generally, it can thus be possible to determine values for at least one imaging parameter of the robotic visualization system which is used for recording the at least one search image sequence, based on prior knowledge. By way of example, a brightness of an illumination could be set as an exemplary imaging parameter. An exposure time could be set as an exemplary imaging parameter. An arrangement of corresponding search regions could be determined. A reuse of search images between different search image sequences could be determined.

Such prior knowledge can concern for example the (rough) arrangement of the patient in relation to the robotic visualization system. Alternatively or additionally, such prior knowledge could also concern the arrangement of the target region in relation to a marker stationarily fixed with respect to the patient. By way of example, specifically the patient can be roughly pre-positioned in relation to the robotic visualization system. By way of example, the patient can be arranged on a patient couch, the arrangement of the patient couch in relation to the robotic visualization system being known. In this way, in a first step, the robotic visualization system could be roughly aligned with the (presumed) position of the patient and, subsequently, the search images of the at least one search image sequence could be captured based on this prior knowledge. The same can also apply to a marker stationarily fixed with respect to the patient.

The method could furthermore comprise evaluating already captured search images of the at least one search image sequence during the recording of the at least one search image sequence. Depending on the evaluating, the recording of the at least one search image sequence could then be selectively terminated, that is to say that capturing further search images can be dispensed with. Alternatively or additionally, it would also be conceivable, depending on the evaluating, to adapt values for at least one imaging parameter of the robotic visualization system which is used for recording the at least one search image sequence.

In other words, if a plurality of search images are captured, then it is possible to continuously check whether it is necessary for further search images to be captured (or whether, for example, the target region has already been recognized and the further capture of search images is thus unnecessary). Furthermore, it would be possible to check whether the values for the at least one imaging parameter are suitably set, or whether an adaptation ought to be carried out, for example an adaptation of the brightness or the exposure time, etc.

In general, the arrangement of the target region can be determined based on structure recognition of one or more predefined structures in the at least one search image. In this regard, for example, the structure of skin tissue could be recognized in the at least one search image. Alternatively or additionally, the structure of specific anatomic features (for example nose, ear, mouth, eye, etc.) could be recognized in the at least one search image. Suitable algorithms can be used. The specific implementation of such an algorithm for determining the arrangement of the target region is not essential to the implementation of the techniques described herein, however, and it is possible to have recourse to previously known implementations.

For recording the at least one search image, for example, an overview-image imaging unit of the robotic visualization system and/or a microscopy imaging unit of the robotic visualization system can be actuated. That means in other words that the at least one search image for example can comprise an overview image with comparatively low magnification and/or can also comprise a microscopy image with comparatively high magnification.

The measurement data can be captured for example with a measurement modality selected from the following group: stereoscopic imaging; time-of-flight measurement; structured illumination; and defocus depth estimation.

In the case of stereoscopic imaging, information about the topography is obtained by means of two cameras that image the same area with different poses.

In the case of time-of-flight measurement, information about the topography can be obtained by means of short light pulses and the corresponding monitoring of the time of flight.

In the case of structured illumination, a predefined pattern, for example a line pattern, is projected onto a surface to be measured. The distortion of the predefined pattern can then be used to obtain information about the topography.

In the case of defocus depth estimation, information about the topography can be obtained through the local use of an autofocusing method.

As a general rule, it would be conceivable for the measurement data to comprise at least one search image. That means that it is not absolutely necessary for the measurement data to be captured completely separately from the search images.

The method could furthermore comprise filtering the measurement data. By way of example, in this case, data elements which do not image skin tissue of the patient could be removed from the measurement data. By way of example, areas which image surgical drapes or markers or surgical instruments could be removed from the measurement data. An erroneous registration of the measurement data in relation to the preoperative volume image data is avoided as a result.

Before the recording of the at least one search image, the motor of the robotic visualization system can be actuated in order to arrange the robotic visualization system in a predefined reference arrangement. By way of example, the predefined reference arrangement could be defined in relation to an operating table. The predefined reference arrangement could be defined for example in such a way that an area of the operating table on which the patient's head is to be arranged lies in the field of view of the imaging unit of the robotic visualization system which is used for recording first the at least one search image.

It would be conceivable for the method furthermore to comprise setting at least one imaging parameter of the robotic visualization system to a predefined value before the recording of the at least one search image. This could comprise for example a setting of a target magnification for a zoom factor of a corresponding imaging unit of the robotic visualization system. A specific brightness of an illumination could be selected. It would be conceivable for the exposure time to be set to a specific value.

A method described herein can be carried out in an automated manner based on a predefined control script. By way of example, the control script can be initiated by means of a single user command (e.g. "one-click"). In this way, it is possible to achieve particularly simple and rapid capture of measurement data, which subsequently makes it possible to determine the transformation specification; manual repositioning of the robotic visualization system can be dispensable.

By way of example, such a control script could comprise an analysis module for evaluating image data or measurement data. Moreover, the control script could comprise at least one positioning module for positioning the robotic visualization system. Such positioning could be used for example to capture, by means of scanning, search images of a search image sequence which cover a search region that is larger than the field of view of an individual search image. The analysis module could evaluate image data for example in order to find skin tissue. The analysis module could evaluate image data for example in order to recognize a marker that is fixed stationarily in relation to the patient.

The analysis module can comprise for example one or more machine-learned algorithms. By way of example, artificial neural networks that recognize predefined structures or objects in images could be used. A convolutional neural network, for example, could be used for this purpose. Corresponding training can be made possible for example by means of manual annotation of corresponding training image data or training measurement data.

On the other hand, it would be conceivable for the positioning module to comprise no machine-learned algorithms. A manually parameterized algorithm can be used. This can be worthwhile in particular because in this way, for each input parameter, the new position of the positioning module of a validation phase can be validated in order to avoid uncontrolled or dangerous movements of the robotic visualization system. The method can furthermore comprise generating a topography data set based on the measurement data. That means that the measurement data can be evaluated, for example by means of an analysis module as described above.

The method can furthermore comprise carrying out a registration of the topography data set with the preoperative volume image data. That means that corresponding points can be found in the topography data set and the preoperative volume image data. The transformation specification can then be determined based on the relative arrangement of such corresponding points with respect to one another. Generally, the transformation specification can be determined based on the registration.

A data processing unit is configured to actuate a robotic visualization system in order to record at least one search image in this way. The at least one search image at least partly images a patient. Moreover, the data processing unit is configured to determine the arrangement of a target region in the at least one search image and, based on this arrangement of the target region in the at least one search image, to actuate the robotic visualization system in order to record measurement data with depth resolution. These measurement data are indicative of a topography of an anatomy of the patient. This makes it possible to determine a transformation specification between images recorded by means of the robotic visualization system and preoperative volume image data of the patient.

A system comprises the data processing unit and the robotic visualization system.

A computer program or a computer program product or a computer-readable storage medium comprises program code. The program code can be loaded and executed by a processor. This causes the processor to carry out a method. The method comprises actuating a robotic visualization system in order to record at least one search image in this way. The at least one search image at least partly images a patient. Moreover, the method also comprises determining an arrangement of a target region in the at least one search image. Furthermore, the method comprises actuating the robotic visualization system for recording measurement data with depth resolution based on the arrangement of the target region in the at least one search image. In this case, the measurement data are indicative of a topography of an anatomy of the patient. The measurement data make it possible to determine a transformation specification between images recorded by means of the robotic visualization system and preoperative volume image data of the patient.

The features set out above and features that are described hereinbelow can be used not only in the corresponding combinations explicitly set out, but also in further combinations or in isolation, without departing from the scope of protection of the present invention.

DETAILED DESCRIPTION OF EMBODIMENTS

The properties, features and advantages of this invention described above and the way in which they are achieved will become clearer and more clearly understood in association with the following description of the exemplary embodiments which are explained in greater detail in association with the drawings.

The present invention is explained in greater detail below on the basis of preferred embodiments with reference to the drawings. In the figures, identical reference signs denote identical or similar elements. The figures are schematic representations of various embodiments of the invention. Elements illustrated in the figures are not necessarily illustrated as true to scale. Rather, the various elements illustrated in the figures are rendered in such a way that their function and general purpose become comprehensible to a person skilled in the art. Connections and couplings between functional units and elements illustrated in the figures can also be implemented as an indirect connection or coupling. A connection or coupling can be implemented in a wired or wireless manner. Functional units can be implemented as hardware, software or a combination of hardware and software.

A description is given below of techniques which make it possible to determine a transformation specification to map or to convert the image data captured by means of a robotic visualization system (simply called surgical microscope hereinafter) to preoperative volume image data; the inverse mapping specification can also be encompassed by the transformation specification.

For this purpose, a target region is automatically recognized or its arrangement is automatically determined, based on one or more search images. It is then possible to determine for this target region measurement data with depth resolution which can be registered in relation to the preoperative volume image data in order to derive the transformation specification from this registration.

Various applications can then be made possible on the basis of this transformation specification. By way of example, a functionality providing assistance to a surgeon could be provided based on the preoperative volume image data and the transformation specification. By way of example, the preoperative volume image data or portions thereof can be inserted in a spatially true manner into a field of view of the surgical microscope or into image data captured by means of the surgical microscope. Specific areas identified in the preoperative volume image data could be highlighted in image data captured by means of the surgical microscope. A navigation assistance functionality that guides the surgical intervention can be made possible.

Figure 1:
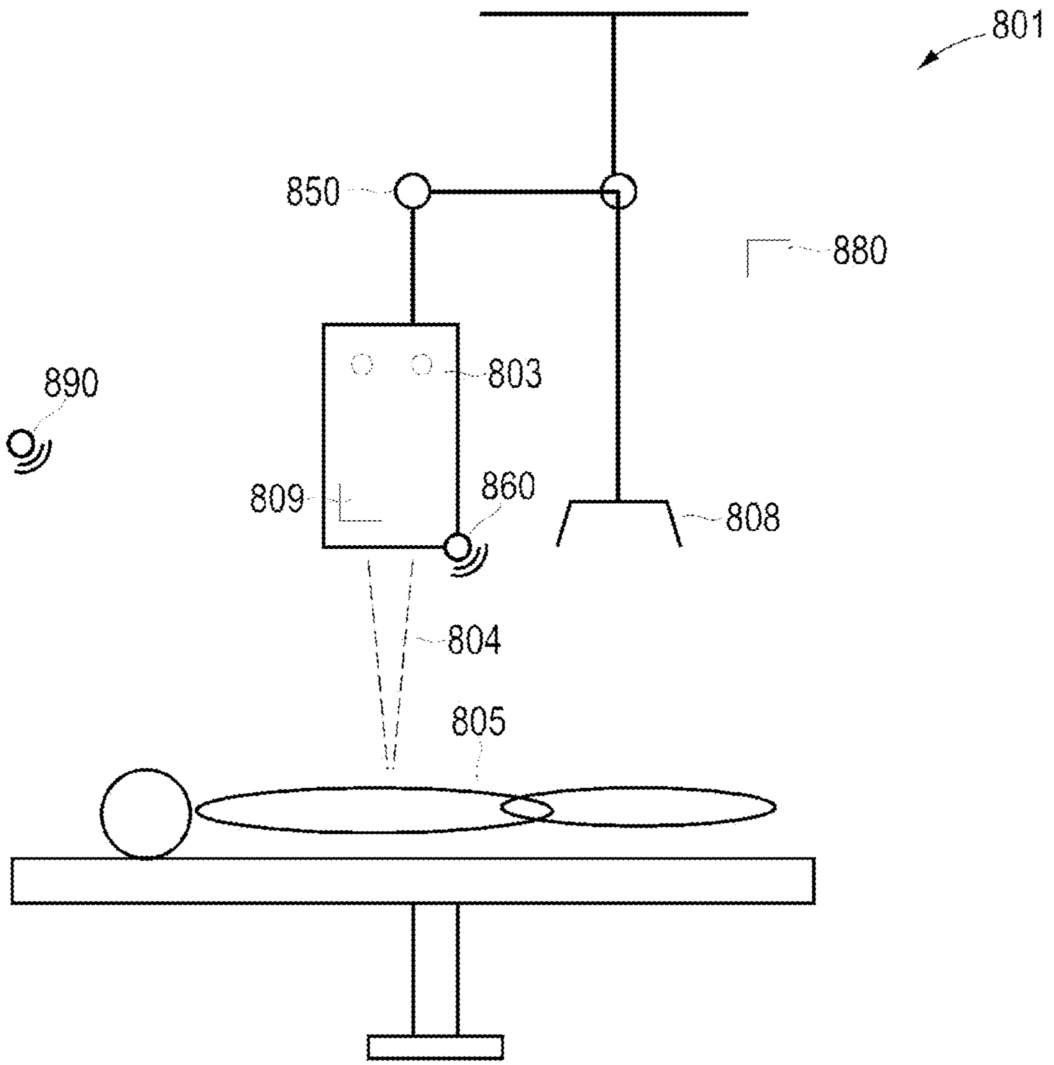
FIG. 1 schematically illustrates an optical visualization system in accordance with various examples.

FIG. 1 schematically shows a surgical microscope 801 for surgery. In the illustrated example, the surgical microscope 801 comprises an eyepiece 803. Through the eyepiece 803, the surgeon can observe magnified images of an object which is situated in a field of view 804 of the surgical microscope 801. In the illustrated example, this is a patient 805 lying on a patient couch.

As an alternative or in addition to an optical eyepiece, provision could also be made of a camera 809 which transmits images to a screen (digital surgical microscope).

Put generally, the surgical microscope 801 can comprise one or more imaging unit configured to record digital images. Examples of an imaging unit would be, for example, a microscopy imaging unit and an overview-image imaging unit. The microscopy imaging unit could include one or two or more cameras; by way of example, stereoscopic imaging could be possible with a plurality of cameras.

An operating device 808 is also provided as a human-machine interface; by way of example, it can be embodied as a handle or a foot switch. It is a handle in the embodiment illustrated in FIG. 1. The operating device 808 allows the eyepiece 803, which is fastened to crossbeams 850, to be moved. Motors can be provided in order to automatically carry out the movement on the basis of control data, in accordance with a corresponding setting of the surgical microscope. The motors could also assist the movement instigated by the handle 808.

Furthermore, a control device 880 is provided for the surgical microscope 801 and controls the operation of the surgical microscope 801 and the display of images and additional information and data in the eyepiece 803. The control device 880 can carry out an interaction with the surgeon.

The surgical microscope 801 can also comprise one or more further sensors 860, for instance an environment camera, a time-of-flight sensor (TOF camera), an image recording device for recording images which are captured in the case of structured illumination, etc.; measurement data having a depth resolution, for example, can be captured by means of such sensors 860. That means that the depth resolution can describe the distance between the corresponding sensor 860 and the patient 805.

A further implementation of such a sensor 860 would concern an internal tracking system. For example, markers that are fixed in relative relation to the patient and are embodied as machine-readable can be recognized by means of such an internal tracking system. Markers are sometimes also referred to as targets. In particular, the relative arrangement of the markers in relation to the surgical microscope 801 can be determined.

FIG. 1 also illustrates an external tracking system 890. The latter is collocated with the surgical microscope 801. It is possible for tracking data 890 to be transmitted from the tracking system 890 to the control device 880, the tracking data being indicative for example of the arrangement of the camera 809 or of the eyepiece 803 or generally of the field of view 804 of an imaging unit in space, for example in relation to markers positioned stationarily in relation to the patient 805, or a spatially fixed reference coordinate system.

Figure 2:
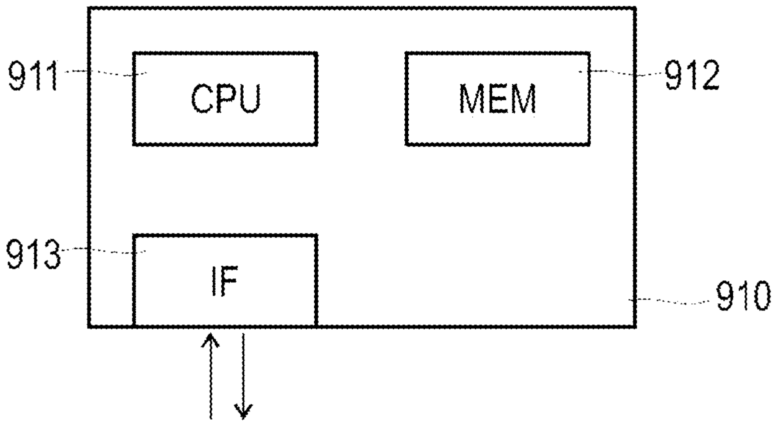
FIG. 2 schematically illustrates a data processing unit in accordance with various examples.

FIG. 2 illustrates aspects in connection with a data processing unit 910. The data processing unit 910 could be implemented by a computer, for example. The data processing unit 910 could implement for example the control device 880 of the surgical microscope 801 (cf. FIG. 1) or could also be embodied separately from the surgical microscope 801 (and then communicate with the control device 880, for example).

The data processing unit 910 comprises a computing unit 911 and a memory 912 and a communication interface 913. The computing unit 911 can for example load program code from the memory 912 and execute said code. The computing unit 911 can communicate with other devices, nodes or apparatuses via the communication interface 913. By way of example, tracking data could be received from a tracking system. It would be possible to receive preoperative volume image data, for example from an image archive system or some other database. User inputs could be received from a human-machine interface.

If the computing unit 911 executes program code loaded from the memory 912, for example, then this can cause the computing unit 911 to implement techniques as described herein, for instance: recording search images or measurement data; evaluating search images or measurement data; determining an arrangement of a target region in search images; actuating the surgical microscope 801 in order to capture images, search images, or measurement data and/or to bring about a specific position of the field of view 804; providing control data in order to enable an assistance functionality for a surgeon; determining a transformation specification between image data captured by means of the surgical microscope 801 and preoperative volume image data, for example based on a corresponding registration between measurement data with depth resolution and the preoperative volume image data. Various functionalities which can be provided and implemented by the computing unit 911 based on corresponding program code are described below in association with the method in FIG. 3.

Figure 3:
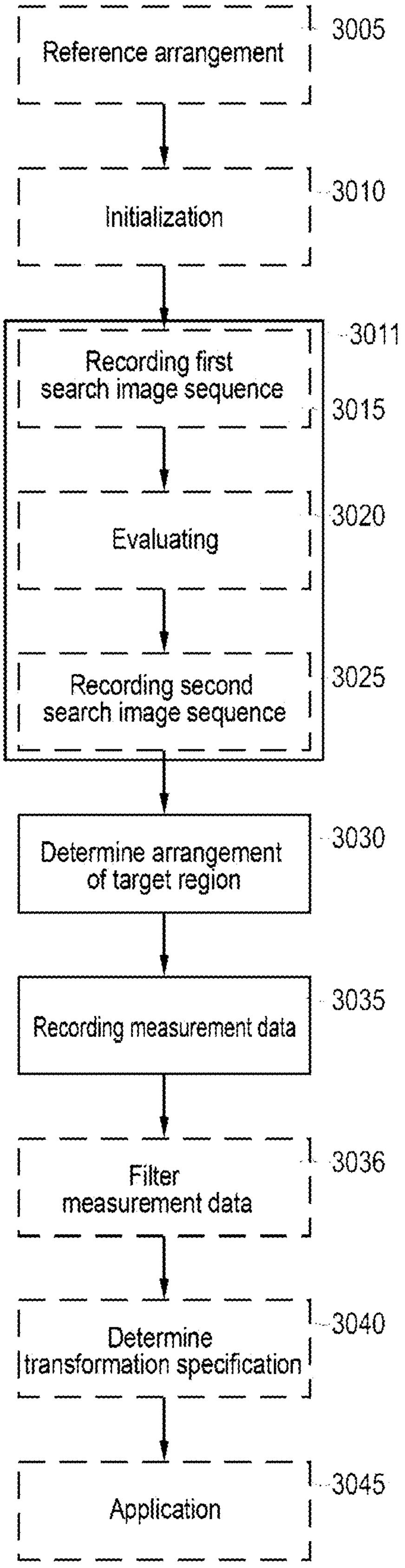
FIG. 3 is a flowchart of one exemplary method.

FIG. 3 is a flowchart of one exemplary method. By way of example, the method in FIG. 3 could be carried out by a data processing unit such as, for example, the data processing unit 910 from FIG. 2. In particular, the method from FIG. 3 could be carried out by a computing unit, for example a processor, when the latter loads and executes program code.

The method in FIG. 3 serves to make it possible to determine a transformation specification between images recorded by means of a surgical microscope and preoperative volume image data—for example CT image data or MRI image data. In other words, the method in FIG. 3 thus serves for calibrating the positioning of the patient in relation to the surgical microscope and relative to the preoperative volume image data. In particular, the method in FIG. 3 supports automated capture of measurement data with depth resolution by the surgical microscope, such that these measurement data can then be registered in relation to the preoperative volume image data. The transformation specification can then be determined based on this registration; however, the transformation specification could also be determined in a downstream method, for example by a different data processing system, for instance by a control device of a tracking system.

By way of example, it would be conceivable for the method in accordance with FIG. 3 to be carried out based on an automated control script. That means that the various method steps can be processed successively by a computer program in an automated manner. This has the advantage that the user can initiate the corresponding control script just by way of a single human-machine interaction, for example, and there is no longer a need for manual interactions during the processing of the corresponding method steps.

Optional boxes are represented using dashed lines in FIG. 3.

Firstly, in box 3005, a motor of the surgical microscope can be actuated in order to arrange the surgical microscope in a predefined reference arrangement. By way of example, this reference arrangement could cause the field of view of the surgical microscope to be aligned with a patient's head area when the patient is arranged on a corresponding couch.

Afterward, in box 3010, it is optionally possible to carry out an initialization of one or more imaging parameters. That means that it would be possible to set at least one imaging parameter of the surgical microscope to a predefined value before the recording of search images. By way of example, the brightness of an illumination could be initialized or it would be conceivable for a magnification factor of a zoom to be set. A predefined focus could be chosen. A specific field of view could be set.

Sometimes box 3010 and box 3005 can also be implemented together. For example if the imaging parameter the positioning of a corresponding imaging unit of the surgical microscope is set in box 3010.

Afterward, box 3011 involves recording at least one search image which at least partly images the patient. For this purpose, the surgical microscope or strictly speaking a corresponding imaging unit or a corresponding control device can be actuated. A command for capturing the corresponding at least one search image can be sent.

For example, an overview-image imaging unit of the surgical microscope and/or a microscopy imaging unit of the surgical microscope could be actuated for recording the at least one search image. That means, therefore, that for example one or more overview images with low magnification and/or one or more microscopy images with high magnification can be used to implement the at least one search image.

There are various implementation variants for box 3011. Before these implementation variants are discussed in detail below, firstly the subsequent method is explained in greater detail.

Box 3030 involves determining an arrangement of a target region in the at least one search image. That means determining a position and/or orientation and/or an extent of a target region in the at least one search image. An analysis module can be used. For this purpose, a machine-learned algorithm could be used, for example. Such a machine-learned algorithm could be trained based on training search images and manual annotations of target regions. The machine-learned algorithm could be implemented by a convolutional neural network, for example.

The target region can denote for example an intervention area of planned surgery. The target region can denote an area of the patient's body for which the preoperative volume image data were captured or which is imaged by the preoperative volume image data.

For example, the arrangement of the target region could be determined based on structure recognition of one or more predefined structures in the at least one search image. For example, skin tissue or anatomic features could be recognized. However, a machine-readable marker could also be recognized.

It is then possible, in box 3035, to capture measurement data with depth resolution based on this arrangement of the target region. For this purpose, the surgical microscope can be actuated, for example a corresponding sensor, a corresponding imaging unit or an assigned control device. The measurement data are thus indicative of a topography of the anatomy of the patient in the area of the target region.

For example, the measurement data could be captured with a measurement modality selected from the group comprising: stereoscopic imaging; time-of-flight measurement; structured illumination; and defocus depth estimation.

In some examples, it would also be possible for the measurement data to comprise at least one of the at least one search image. That means, therefore, that it would be conceivable for specific images not only to be used as search images in box 3011, but also to be taken into account in the context of the measurement data in box 3035, i.e. to fulfil a double function.

In box 3036, it would optionally be possible to filter the measurement data. By way of example, noise suppression could be carried out. Background could be removed. It would be possible to remove data elements which do not image skin tissue of the patient.

In this way, it can be possible to determine the transformation specification between images recorded by means of the surgical microscope and preoperative volume image data of the patient. This transformation specification can be determined in optional box 3040. It would also be possible to store the measurement data for a later determination or to communicate them to a different data processing unit, such that the latter determines the transformation specification.

If the transformation specification is determined, then this can be done as follows: firstly a topography data set can be generated based on the measurement data. That means that, for example, a height profile of the patient's head or generally of the skin surface of the patient in the target region can be determined. A registration of this topography data set with the preoperative volume image data can then be carried out. Specifically, the preoperative volume image data can in particular also image the topography of the skin surface of the patient's head. Based on this registration, the transformation specification can then be determined, for example taking account of translational and/or rotational degrees of freedom. Distortions can also be taken into account.

Optionally, an application based on this transformation specification can be enabled in box 3045. By way of example, computer-assisted surgery could be enabled, for instance in the context of augmented images which are captured by means of the surgical microscope and have information determined on the basis of the preoperative volume image data. A navigation assistance functionality is enabled.

Figure 4:
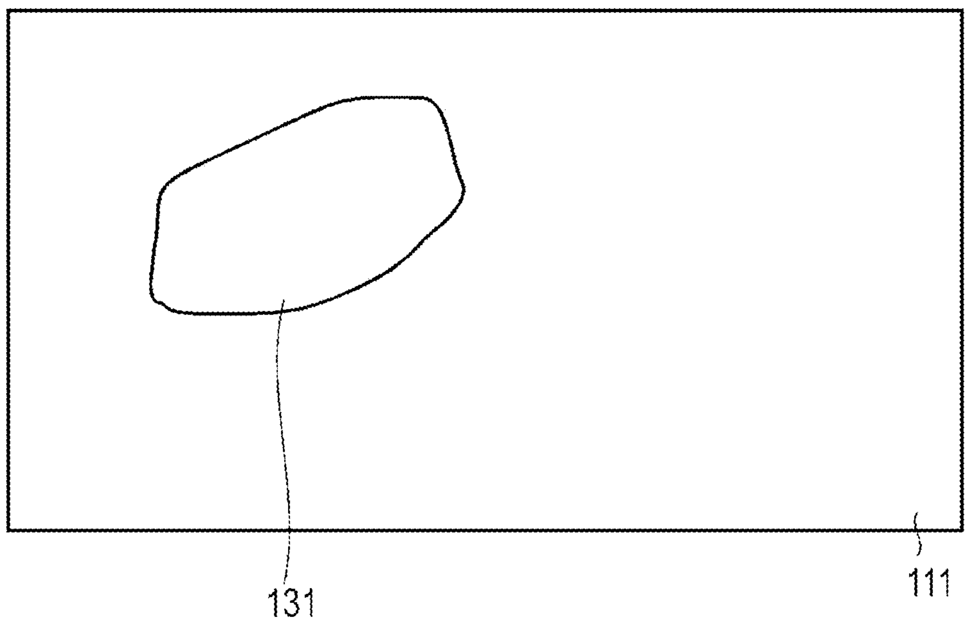
FIG. 4 illustrates an individual search image and a target region in accordance with various examples.

Details in connection with box 3011, namely with recording at least one search image, are described below. In one simple variant, it would be possible to record a single search image and to determine the arrangement of the target region in the single search image. Such a scenario is illustrated in FIG. 4. FIG. 4 illustrates a search image 111. The search image 111 images the target region 131. By way of example, the search image 111 could be captured by an overview-image imaging unit of the surgical microscope 801 (cf. FIG. 1).

Figure 5:
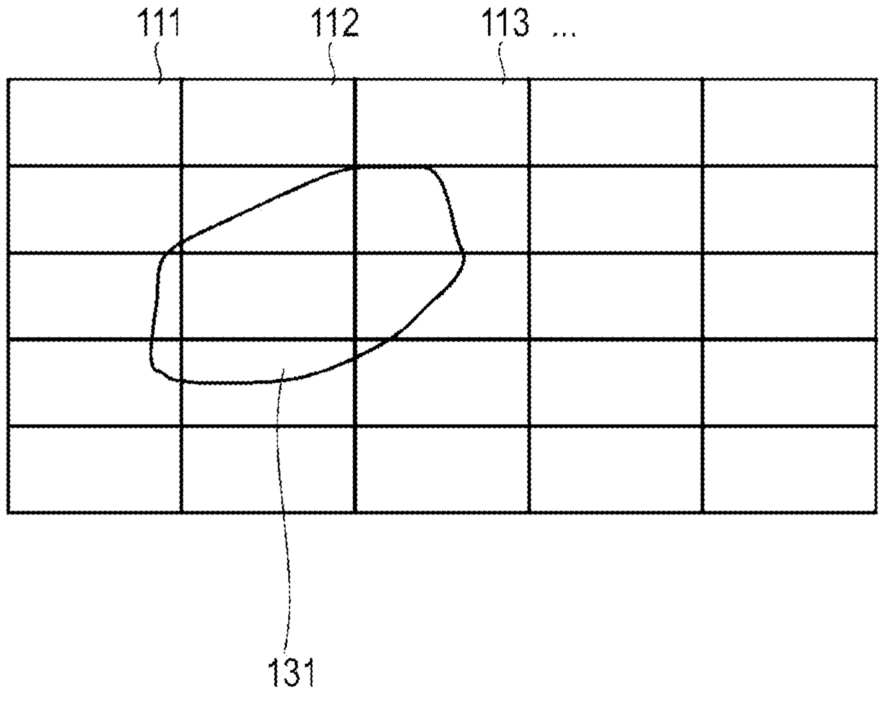
FIG. 5 illustrates a search image sequence and a target region in accordance with various examples.

In another variant, one or more search image sequences could also be captured. By way of example, FIG. 5 shows a scenario in which a total of 25 search images 111-113 (only the first three search images are provided with reference signs, for reasons of clarity) are captured. By way of example, each of these search images of the search image sequence could have a particularly high resolution. High magnifications can also be made possible in this way. This corresponds to scanning a corresponding search region. The scanning can be achieved by actuating a motor of the surgical microscope, such that the surgical microscope is repositioned a number of times, for example between the capture of the various search images of the search image sequence.

In some examples, a plurality of search image sequences could also be captured successively. Such a scenario is described in FIG. 3 in connection with box 3011. In this case, firstly, a first search image sequence, to which a first search region is assigned, is recorded in box 3015; and then a second search image sequence, to which a second search region is assigned, is recorded in box 3025. In between it is possible, in box 3020, to evaluate one or more search images of the first search image sequence from box 3015 and, based on this evaluating, to determine values for at least one imaging parameter of the surgical microscope which is used for recording the second search image sequence in subsequent box 3025.

This evaluating in box 3020 could comprise for example determining an arrangement of a marker stationarily fixed with respect to the patient in the one or more search images of the first search image sequence from box 3015.

This would make it possible to determine for example the arrangement of the second search region, for which the second search image sequence is captured in box 3025, in relation to the first search region of the first search image sequence from box 3015. It would also be possible to ascertain whether a search image of the first search image sequence is reused for the second search image sequence. It would be possible to set for example an illumination parameter for the recording of the second search image sequence. It would be possible to set a magnification factor for the search images of the second search image sequence.

If a plurality of search image sequences are used—as illustrative for example in FIG. 3 in connection with box 3015 and box 3025—then it is possible, in principle, for at least one search image to be part of a plurality of search image sequences.

A description is given below, in TAB. 1, of a workflow which can implement the method in FIG. 3.

TABLE 1 exemplary implementation of a workflow that makes it possible to determine a transformation specification between images captured by means of a surgical microscope and preoperative volume image data. The steps need not necessarily be carried out rigidly in this order, but rather can also be combined or run in parallel so as, if appropriate, to reuse data that have already been recorded.

| Step | Brief description | Exemplary details |
|---|---|---|
| 1 | Start control script | Firstly, the user starts the registration of the patient by way of a command, e.g. pressing a button, foot switch panel, voice, . . . That means that a corresponding control script which automatically carries out the subsequent steps is started. |
| 2 | Rough alignment | The surgical microscope is positioned in a reference arrangement, for example pointing straight down at a head area of a couch. For this purpose, a motor can be actuated accordingly. The robotic surgical microscope is automatically aligned such that the environment camera is oriented in the negative z-direction (points downward) and the possible working distance is maximized. Alternatively or additionally, a different camera, e.g. a camera of a microscopy imaging unit, could also be oriented in the negative z-direction. The surgical microscope is then brought "roughly" over the patient, i.e. it can be assumed that the cameras of the surgical microscope is situated above the patient as viewed spatially in the z-direction (orthogonally from the floor upward). Cf. FIG. 3: box 3005. |

TABLE 1-continued exemplary implementation of a workflow that makes it possible to determine a transformation specification between images captured by means of a surgical microscope and preoperative volume image data. The steps need not necessarily be carried out rigidly in this order, but rather can also be combined or run in parallel so as, if appropriate, to reuse data that have already been recorded.

TABLE 1-continued exemplary implementation of a workflow that makes it possible to determine a transformation specification between images captured by means of a surgical microscope and preoperative volume image data. The steps need not necessarily be carried out rigidly in this order, but rather can also be combined or run in parallel so as, if appropriate, to reuse data that have already been recorded.

| Step | Brief description | Exemplary details |
|---|---|---|
| 3 | Initialization | Then—if settable—the zoom factor of the environment camera is automatically set to the minimum beforehand. Optionally, the light source of the surgical microscope is switched into a sensitive mode in order to protect the patient's eye (the lid being assumed to be closed). In other words, the light intensity is set to a comparatively low value.<br>The zoom factor and the brightness of the illumination are just two examples of imaging parameters which can be set to a predefined value in order to achieve an initialization.<br>Cf. FIG. 3: box 3010. |
| 4 | Recognizing markers | The approximate position of the patient's head is then determined. For this purpose, search images of an environment camera (i.e. of an overview-image imaging unit) are evaluated as to whether a marker which is attached to the patient's head or is stationarily fixed with respect thereto (for example on a Mayfield clamp or a ring that is rigidly connected to the clamp) is visible.<br>A microscopy imaging unit could also be used instead of the environment camera. By way of example, stereoscopic search images could be captured.<br>That is to say that a first search image sequence is recorded.<br>Afterward, the surgical microscope—with simultaneous image evaluation—carries out a scanning movement (e.g. spirally outward) in the xy plane until it has been possible to find the marker in the image and to determine its position relative to the tracking camera or generally in relation to the surgical microscope. Other scan patterns for scanning a search region are conceivable. Generally, 2D or 3D scan patterns are conceivable. Further examples would be spherical patterns or patterns comprising a pivot movement.<br>Optionally, it would be conceivable, during the recording of the search images, to constantly identify whether the patient's eye is open. If affirmative, the scanning process is automatically interrupted/terminated or the light for the area of the eye is switched off.<br>Cf. FIG. 3: boxes 3015, 3020.<br>Sometimes it is conceivable for the relative positioning of the surgical microscope in relation to a marker to be known already, for example based on tracking data received from a tracking system. In that case it is not necessary to capture search images of a corresponding search image sequence for the purpose of determining the arrangement of the marker, rather the arrangement of the marker can be determined based on the tracking data. |
| 5 | Recognizing patient's head as target region | With the knowledge of where the marker is situated in space, a search is then made to find the position of the patient's head in a defined volume around the marker. The corresponding search region is thus determined based on the arrangement of the marker in space, and determined based on prior knowledge concerning the typical head size in all spatial directions around the marker. Generally, values for at least one imaging parameter for the recording of search images can be determined based on prior knowledge concerning an arrangement of the patient in relation to the surgical microscope and/or an arrangement of the target region in relation to a marker.<br>Optionally, the search region for this second search image sequence can be delimited by knowledge of how the patient is lying and the attachment of the marker (whether on the right, on the left, on top, underneath, etc.).<br>The surgical microscope scans the search region (or uses at least one portion of the search images from step 4).<br>An analysis module recognizes the patient's head as target region. For this purpose, for example, by way of image processing of the analysis module (e.g. machine learning approaches), skin tissue or specific anatomies (for instance mouth, nose or eye sockets) is/are automatically recognized in the image.<br>Supplementarily or alternatively, topography data (i.e. measurement data with depth resolution) are also created, such that the three-dimensional data can be matched against a typical shape of the human skull and thus yield an additional indication for recognizing the patient's head.<br>Cf. FIG. 3: boxes 3025, 3030 . . . |
| 6 | Measurement data | Once the position or generally the arrangement of the patient's head is known as target region, the topography of the patient's head is captured. For this purpose, measurement data having a depth resolution are recorded.<br>Optionally, scanning can be effected here, too, i.e. it is possible to use an automatic movement of the surgical microscope for the stitching of the field of view. It would be conceivable to reuse search images from step 4 or 5 in order to reduce the scanning time.<br>Cf. FIG. 3: box 3035. |
| 7 | Filtering | The measurement data are optionally (automatically) correctively adjusted, i.e. regions with non-skin tissue (e.g. drapes) are removed and/or metallic mounts/instruments are removed as well.<br>This is done either by way of the evaluation of an image contrast (automatic recognition of skin tissue) and/or by way of the topographic information (e.g. structures which are not directly linked to the skull and are at a distance of >5 cm are removed).<br>Cf. FIG. 3: box 3036. |
| 8 | Transformation specification | The ascertained topography is used for the registration of the patient and, for example, sent to a navigation system.<br>Cf. FIG. 3: box 3040. |

In summary, a description has been given above of techniques which make possible an automatic recognition of an area to be scanned for the registration of the patient, that is to say of a target region. An automatic alignment of a robotic visualization system, such that measurement data which have a depth resolution and image the target region can be captured, has been disclosed.

It goes without saying that the features of the embodiments and aspects of the invention described above can be combined with one another. In particular, the features can be used not only in the combinations described but also in other combinations or on their own, without departing from the scope of the invention.

The invention claimed is:

1. A computer-implemented method, comprising:

actuating a robotic visualization system that includes a surgical microscope for recording search images which at least partly depict a patient, wherein the robotic visualization system is actuated in order to record at least two search image sequences, wherein each of the at least two search image sequences comprises a plurality of corresponding search images, during the recording of the at least two search image sequences, actuating at least one motor of the robotic visualization system in order to reposition the robotic visualization system multiple times, such that the plurality of search images of the respective search image sequence scan a search region assigned to the respective search image sequence, wherein a first search region is assigned to a first search image sequence of the at least two search image sequences, wherein a second search region is assigned to a second search image sequence of the at least two search image sequences, wherein the robotic visualization system is first actuated for recording the first search image sequence and is subsequently actuated for recording the second search image sequence, evaluating one or more of the search images of the first search image sequence and, based on evaluating the one or more of the search images of the first search image sequence, determining values for at least one imaging parameter of the robotic visualization system which is used for recording the second search image sequence, determining an arrangement of a target region in at least one of the search images, based on the arrangement of the target region in the at least one of the search images, actuating the robotic visualization system for recording measurement data with depth resolution, wherein the measurement data is indicative of a topography of an anatomy of the patient, based on the topography of the anatomy of the patient, determining a transformation specification between images recorded by the robotic visualization system and preoperative volume image data of the patient, and controlling the surgical microscope to capture images during surgery and implementing computer-assisted surgery by superimposing the preoperative volume image data and the captured images based on the transformation specification.

2. The computer-implemented method as claimed in claim 1, wherein evaluating the one or more of the search images of the first search image sequence comprises determining an arrangement of a marker stationarily fixed with respect to the patient in the one or more of the search images of the first search image sequence, and wherein the values for the at least one imaging parameter are determined based on the arrangement of the marker stationarily fixed with respect to the patient.

3. The computer-implemented method as claimed in claim 1, wherein the at least one imaging parameter comprises an arrangement of the second search region in relation to the first search region.

4. The computer-implemented method as claimed in claim 1, wherein the at least one imaging parameter comprises an illumination parameter for recording the second search image sequence.

5. The computer-implemented method as claimed in claim 1, wherein the method further comprises:

evaluating one or more of the search images of the second search image sequence for recognizing skin tissue of the patient in the one or more of the search images of the second search image sequence, wherein the arrangement of the target region is determined based on recognizing the skin tissue.

6. The computer-implemented method as claimed in claim 1, wherein the method further comprises:

receiving tracking data from a tracking system collocated with respect to the robotic visualization system, wherein the tracking data describes an arrangement of a marker stationarily fixed with respect to the patient in relation to the robotic visualization system, and determining values for at least one imaging parameter of the robotic visualization system which is used for recording one or more of the at least two search image sequences, based on the tracking data.

7. The computer-implemented method as claimed in claim 1, wherein the method further comprises:

determining values for at least one imaging parameter of the robotic visualization system which is used for recording one or more of the at least two search image sequences based on prior knowledge concerning at least one of an arrangement of the patient in relation to the robotic visualization system and an arrangement of the target region in relation to a marker stationarily fixed with respect to the patient.

8. The computer-implemented method as claimed in claim 1, wherein the method further comprises:

during said recording of one or more of the at least two search image sequences, evaluating already captured search images of the one or more of the at least two search image sequences, and depending on said evaluating, terminating said recording of the one or more of the at least two search image sequences and/or adapting values for at least one imaging parameter of the robotic visualization system which is used for recording the one or more of the at least two search image sequences.

9. The computer-implemented method as claimed in claim 1, wherein the arrangement of the target region is determined based on structure recognition of one or more predefined structures in the at least one of the search images, wherein the one or more predefined structures include skin tissue, anatomic features, or both.

10. The computer-implemented method as claimed in claim 1, wherein at least one of an overview-image imaging unit of the robotic visualization system and a microscopy imaging unit of the robotic visualization system is actuated for recording the at least one of the search images.

11. The computer-implemented method as claimed in claim 1, wherein the measurement data is captured with a measurement modality selected from the following group: stereoscopic imaging; time-of-flight measurement; structured illumination; and defocus depth estimation.

12. The computer-implemented method as claimed in claim 1, wherein the method further comprises:

filtering the measurement data to remove data elements which do not represent skin tissue of the patient.

13. The computer-implemented method as claimed in claim 1, wherein the method further comprises:

actuating a motor of the robotic visualization system to arrange the robotic visualization system in a predefined reference arrangement before the recording of the at least one of the search images.

14. The computer-implemented method as claimed in claim 1, wherein the method further comprises:

setting at least one imaging parameter of the robotic visualization system to a predefined value before the recording of the at least one of the search images.

15. The computer-implemented method as claimed in claim 1, wherein the method is carried out in an automated manner based on a control script.

16. The computer-implemented method as claimed in claim 1, wherein an analysis module for evaluating image data or measurement data comprises one or more machine-learned algorithms, wherein a positioning module for positioning the robotic visualization system does not use a machine-learned algorithms.

17. The computer-implemented method as claimed in claim 1, wherein the method further comprises:

generating a topography data set based on the measurement data, carrying out a registration of the topography data set with the preoperative volume image data, and based on the registration, determining the transformation specification.

18. The computer-implemented method of claim 1, wherein a value of at least one of a zoom of the surgical microscope, focus, lighting, or an arrangement of the second search region covered by the second search image sequence is changed upon recording the first search image sequence and before recording the second search image sequence, said value being changed so that the measurement data is captured more rapidly.

19. A data processing unit, configured to carry out the following steps:

actuating a robotic visualization system that includes a surgical microscope for recording search images which at least partly depict a patient, wherein the robotic visualization system is actuated in order to record at least two search image sequences, wherein each of the at least two search image sequences comprises a plurality of corresponding search images, during the recording of the at least two search image sequences, actuating at least one motor of the robotic visualization system in order to reposition the robotic visualization system multiple times, such that the plurality of search images of the respective search image sequence scan a search region assigned to the respective search image sequence, wherein a first search region is assigned to a first search image sequence of the at least two search image sequences, wherein a second search region is assigned to a second search image sequence of the at least two search image sequences, wherein the robotic visualization system is first actuated for recording the first search image sequence and is subsequently actuated for recording the second search image sequence, evaluating one or more of the search images of the first search image sequence and, based on evaluating the one or more of the search images of the first search image sequence, determining values for at least one imaging parameter of the robotic visualization system which is used for recording the second search image sequence, determining an arrangement of a target region in at least one of the search images, and based on the arrangement of the target region in the at least one of the search images, actuating the robotic visualization system for recording measurement data with depth resolution, wherein the measurement data is indicative of a topography of an anatomy of the patient, based on the topography of the anatomy of the patient, determining a transformation specification between images recorded by the robotic visualization system and preoperative volume image data of the patient, and controlling the surgical microscope to capture images during surgery and implementing computer-assisted surgery by superimposing the preoperative volume image data and the captured images based on the transformation specification.

20. A system, comprising:

the data processing unit as claimed in claim 19, and the robotic visualization system.

* * * * *